(12) United States Patent
Burke et al.

(10) Patent No.: US 12,064,535 B2
(45) Date of Patent: Aug. 20, 2024

(54) POROUS MEDICAL DEVICE AND METHODS OF USE

(71) Applicant: Boston Scientific Scimed, Inc., Maple Grove, MN (US)

(72) Inventors: Martin Burke, Ballybrit (IE); Daniel Tuck, Ballybrit (IE); John T. Favreau, Spencer, MA (US); Lauren Lydecker, Millbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 169 days.

(21) Appl. No.: 17/184,713

(22) Filed: Feb. 25, 2021

(65) Prior Publication Data

US 2021/0268155 A1  Sep. 2, 2021

Related U.S. Application Data

(60) Provisional application No. 62/982,860, filed on Feb. 28, 2020.

(51) Int. Cl.

| | | |
|---|---|---|
| *A61L 31/14* | (2006.01) | |
| *A61L 31/04* | (2006.01) | |
| *A61L 31/12* | (2006.01) | |
| *A61L 31/16* | (2006.01) | |
| *B33Y 70/00* | (2020.01) | |
| *B33Y 80/00* | (2015.01) | |

(52) U.S. Cl.
CPC .......... *A61L 31/146* (2013.01); *A61L 31/041* (2013.01); *A61L 31/125* (2013.01); *A61L 31/16* (2013.01); *B33Y 70/00* (2014.12); *B33Y 80/00* (2014.12); *A61L 2300/406* (2013.01); *A61L 2300/414* (2013.01); *A61L 2400/12* (2013.01)

(58) Field of Classification Search
CPC ...... A61F 13/00068; A61F 2013/00255; A61F 13/00063; A61M 1/84; A61L 31/146
See application file for complete search history.

(56) References Cited

U.S. PATENT DOCUMENTS

| | | | |
|---|---|---|---|
| 5,599,352 A * | 2/1997 | Dinh | A61L 31/046 |
| | | | 623/921 |
| 5,636,643 A | 6/1997 | Argenta et al. | |
| 6,596,296 B1 * | 7/2003 | Nelson | A61P 35/00 |
| | | | 514/772.3 |
| 9,101,515 B2 | 8/2015 | Odermatt et al. | |
| 10,058,413 B2 | 8/2018 | Heiss | |
| 10,232,097 B2 | 3/2019 | Burdick | |
| 10,779,928 B2 | 9/2020 | Heiss | |
| 2007/0219471 A1 | 9/2007 | Johnson et al. | |
| 2007/0282310 A1 | 12/2007 | Bengtson et al. | |
| 2010/0081672 A1 * | 4/2010 | Wan | A61K 9/2027 |
| | | | 514/412 |
| 2011/0270205 A1 * | 11/2011 | Odermatt | A61F 13/15211 |
| | | | 604/374 |
| 2013/0237959 A1 * | 9/2013 | O'Dea | A61M 37/0069 |
| | | | 604/113 |
| 2014/0148839 A1 * | 5/2014 | Pavcnik | A61B 17/1219 |
| | | | 606/191 |
| 2015/0148785 A1 * | 5/2015 | Kleiner | A61M 1/84 |
| | | | 604/543 |
| 2019/0105432 A1 | 4/2019 | Zink et al. | |
| 2020/0276056 A1 | 9/2020 | Leeds | |

FOREIGN PATENT DOCUMENTS

| | | | | |
|---|---|---|---|---|
| EP | 2851102 A1 * | 3/2015 | .......... | A61M 1/0088 |
| EP | 2851102 A1 | 3/2015 | | |
| EP | 3134143 A1 | 3/2017 | | |
| WO | 2015/164801 A1 | 10/2015 | | |
| WO | 2019059893 A1 | 3/2019 | | |

OTHER PUBLICATIONS

Wang et al (International Journal of Nanomedicine, 2017, vol. 12, pp. 1227-1249) (Year: 2017).*

* cited by examiner

*Primary Examiner* — Mark V Stevens
(74) *Attorney, Agent, or Firm* — Bookoff McAndrews, PLLC

(57) ABSTRACT

A medical system including a tube defining a lumen, a porous body connected to a distal end of the tube to be advanced to a target site within a subject. The porous body defines a plurality of openings, the plurality of openings are in fluid connection with the lumen, the porous body includes a first material and a second material, and the second material elutes from the porous body in the subject.

20 Claims, 2 Drawing Sheets

POROUS MEDICAL DEVICE AND METHODS OF USE

CROSS-REFERENCE TO RELATED APPLICATIONS

This application claims the benefit of priority from U.S. Provisional Application No. 62/982,860, filed on Feb. 28, 2020, which is incorporated by reference herein in its entirety.

TECHNICAL FIELD

This disclosure relates to minimally invasive (e.g., endoscopic and/or laparoscopic) medical devices and related methods of use. In embodiments, the disclosure relates to one or more devices for removing fluids, debris, and other materials from perforations, leaks, or wounds in the gastrointestinal tract, methods for forming such device, and related methods of use, among other aspects.

BACKGROUND

Endoscopic and open surgical procedures of the gastrointestinal (GI) tract include, for example, colonic resection, bariatric surgery, esophagectomy, gastric bypass, and sleeve gastrectomy, among others. These procedures may result in perforation, post-surgical leaks, or other wounds of the tract. Limited treatment options exist for managing such wounds, which have significant morbidity and mortality rates. Options include surgical re-operation and endoscopic placement of a stent or clips. Surgery is relatively invasive and also has high morbidity and mortality rates. Endoscopic stent placement is a less invasive option. The placed stent, however, can migrate from the intended location and/or wall off infection at the treatment site, inhibiting drainage.

SUMMARY OF THE DISCLOSURE

According to an aspect, a medical system includes a tube defining a lumen and a porous body connected to a distal end of the tube and configured to be advanced to a target site within a subject. The porous body defines a plurality of openings, wherein the plurality of openings are in fluid connection with the lumen, wherein the porous body includes a first material and a second material, and wherein the second material is configured to elute from the porous body in the subject.

The first material may include a polymer, and the second material may include one or more of a growth factor or an antibiotic.

The first material may include a hygroscopic material, and the porous body may be configured to be in a compressed state during insertion to the target site.

The porous body may be configured to expand from the compressed state to an expanded state when the porous body contacts fluid.

The first material may include a thermoresponsive material, and the porous body may be configured to be in a compressed state during insertion to the target site.

The porous body may be configured to expand from the compressed state to an expanded state when the porous body is heated to a temperature above a temperature threshold.

The plurality of openings may be fluidly disconnected from each other when the porous body is in the compressed state, and the plurality of openings may be in fluid connection as the porous body expands from the compressed state to the expanded state.

The porous body may include nanoparticles having antimicrobial properties.

The plurality of openings may be formed using a crystalline material, and a size and a shape of the openings may be approximately equal to a size and a shape of a crystal of the crystalline material.

The system may further comprise a vacuum source, wherein the vacuum source may be connected to the tube and may be configured to supply a negative pressure to the lumen of the tube and the porous body.

According to another aspect, a method of manufacturing the system may include mixing a polymer with a reagent to form a mixture, forming the porous body using the mixture, and attaching the porous body to the tube using one or more of sutures, or an adhesive, or forming the porous body directly on the tube.

The porous body may be formed using one or more of three-dimensional (3D) printing or electrospinning.

A size of the plurality of openings may be approximately 50 μm to approximately 1 mm in diameter The method may further comprise coating the porous body with an antimicrobial material.

The method may further comprise compressing the porous body from an expanded configuration to a compressed configuration after the porous body is attached to the tube.

According to yet another embodiment, a method of manufacturing a porous body for a medical system comprises creating a mixture of a water-insoluble material and a water-soluble material, curing the mixture, immersing the cured mixture into a water bath, and removing a scaffold from the water bath, wherein the scaffold includes the water insoluble material.

Immersing the cured mixture in the water bath may form a plurality of openings in the scaffold to create the porous body.

The water-soluble material may include a crystal, and a size of the plurality of openings may be substantially equal to a size of the crystal.

The method may further comprise coating the scaffold with a plurality of nanoparticles including an antimicrobial agent.

The method may further comprise dehydrating the scaffold, causing the scaffold to transform from an expanded configuration to a compressed configuration.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
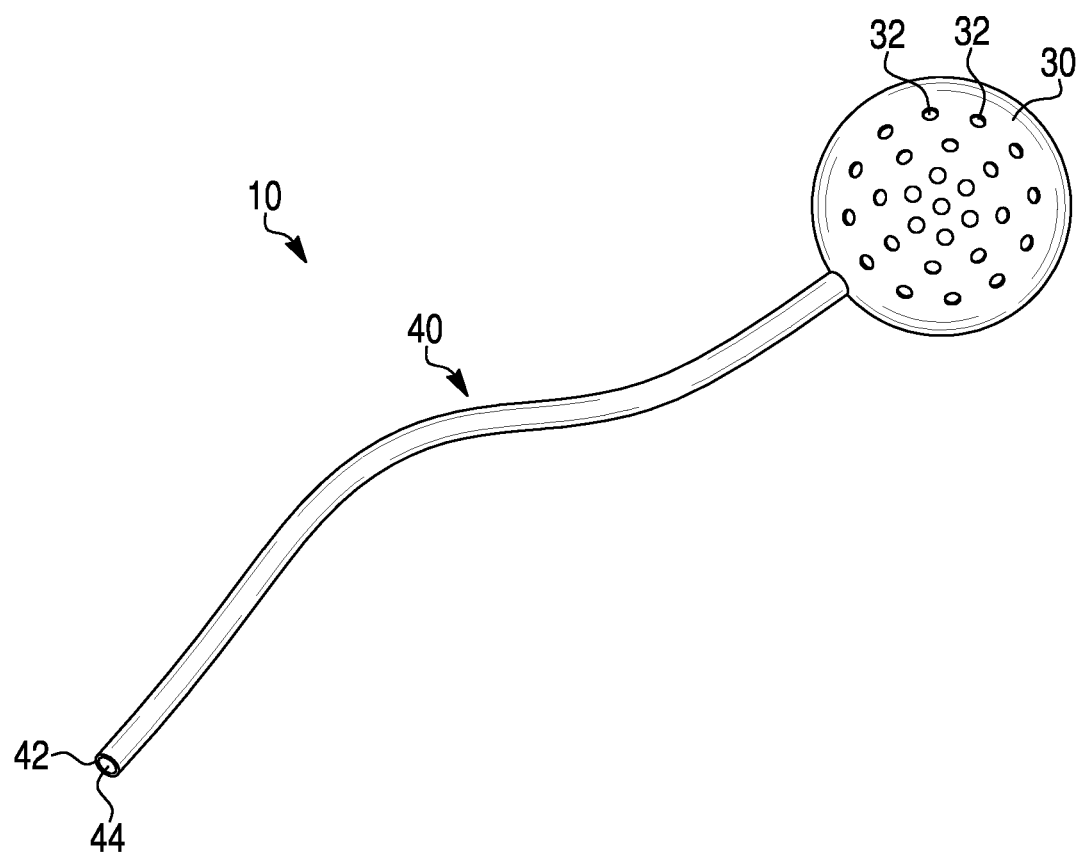
FIG. 1 is a schematic view of an endoluminal vacuum therapy (EVAC) system according to an embodiment.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, "extends distally" indicates that a component extends in a distal direction, and "extends proximally" indicates that a component extends in a proximal direction. Further, as used herein, the terms "about," "approximately," and "substantially" indicate a range of values within +/−10% of a stated or implied value. Terms that indicate the geometric shape of a component/surface refer to exact and approximate shapes. This disclosure may be understood with reference to the following description and the appended drawings, wherein like elements are referred to with the same reference numerals.

Endoluminal vacuum therapy (EVAC) has been proposed. In EVAC, negative pressure is delivered to the wound site in the GI tract, for example through a nasogastric tube having a sponge or porous body at its terminal end. The sponge is placed endoscopically into the perforation, leak, or other wound. Negative pressure then is applied. Devices and systems suited for EVAC are limited, however.

Embodiments of this disclosure include devices, systems, and methods for endoluminal vacuum therapy (EVAC), and formation of devices for performing EVAC. In examples, EVAC includes endoluminal placement of a sponge or other like material into the wound site (e.g., a target site), including a perforation, a cyst, a leak, an anastomosis, etc. Placement of the material may be via a catheter, scope (endoscope, bronchoscope, colonoscope, duodenoscope, gastroscope, etc.), tube, or sheath, inserted into the GI tract via a natural orifice. The orifice can be, for example, the nose, mouth, or anus, and the placement can be in any portion of the GI tract, including the esophagus, stomach, duodenum, large intestine, or small intestine. Placement of the material also can be in other organs (e.g., pancreas) reachable via the GI tract.

FIG. 1 illustrates a distal end of an EVAC system 10 in accordance with an example of this disclosure. System 10 may be inserted into a patient for treatment of chronic wounds using negative pressure via a vacuum. System 10 generally includes a sponge 30 (or other mesh-like material or porous body) and a vacuum tube 40. Sponge 30 is attached to a distal end of vacuum tube 40. Vacuum tube 40 may include an outer wall 42 defining one or more lumens 44. Lumen 44 is open at both a proximal end and the distal end of vacuum tube 40. Outer wall 42 may include a plurality of holes around a circumference of the distal end of vacuum tube 40 and in fluid communication with lumen 44, which may increase the flow of fluid or material into lumen 44, as disclosed herein. The distal end of vacuum tube 40 may be attached to sponge 30 via sutures, an adhesive, or the like. In one example, a recess (not shown) may be provided in sponge 30 to receive the distal end of vacuum tube 40. Vacuum tube 40 may be attached within the recess of sponge 30, which may provide additional structural support between sponge 30 and vacuum tube 40. Alternatively, sponge 30 may be formed on vacuum tube 40, as described herein. The proximal end of vacuum tube 40 may be connected to a vacuum source (not shown), which may supply a negative pressure to sponge 30. For example, a negative pressure of approximately 125 mm Hg, or approximately 2.5 pounds per square inch (PSI), may be supplied to sponge 30. Other suitable amounts of negative pressure may be used. This negative pressure may pull fluid, material, and/or other debris into lumen 44 of vacuum tube 40 via openings 32, which may promote healing of target site 70 (FIG. 2).

Sponge 30 may include openings 32 on an outer surface thereof. Openings 32 may be any hole, pore, or channel which provide continuous access to interconnecting channels and pores throughout sponge 30. Openings 32 may include different sizes and shapes, and may be selected based on a location of treatment within the body. For example, openings 32 may be spherical, cuboidal, irregular, or any other shape. The size of openings 32 may be approximately 50 μm to approximately 1 mm in diameter. Sponge 30 is illustrated as having a spherical shape, but may be any shape, including cylindrical, cuboidal, irregular, or the like. Sponge 30 may also include materials (e.g., a reagent) that are eluted from sponge 30 when deployed at target site 70, as described herein. According to an example, the reagent may elute at different rates and may be customizable based on various factors, including the anticipated lifetime of sponge 30, the amount of time between replacing sponge 30 with a new sponge 30, etc. Additionally, or alternatively, sponge 30 may be coated with nanoparticles having microbial properties, including silver nanoparticles or the like which may improve the activity of the materials eluted from sponge 30 by altering a membrane permeability of cells and/or improving drug delivery.

Figure 2:
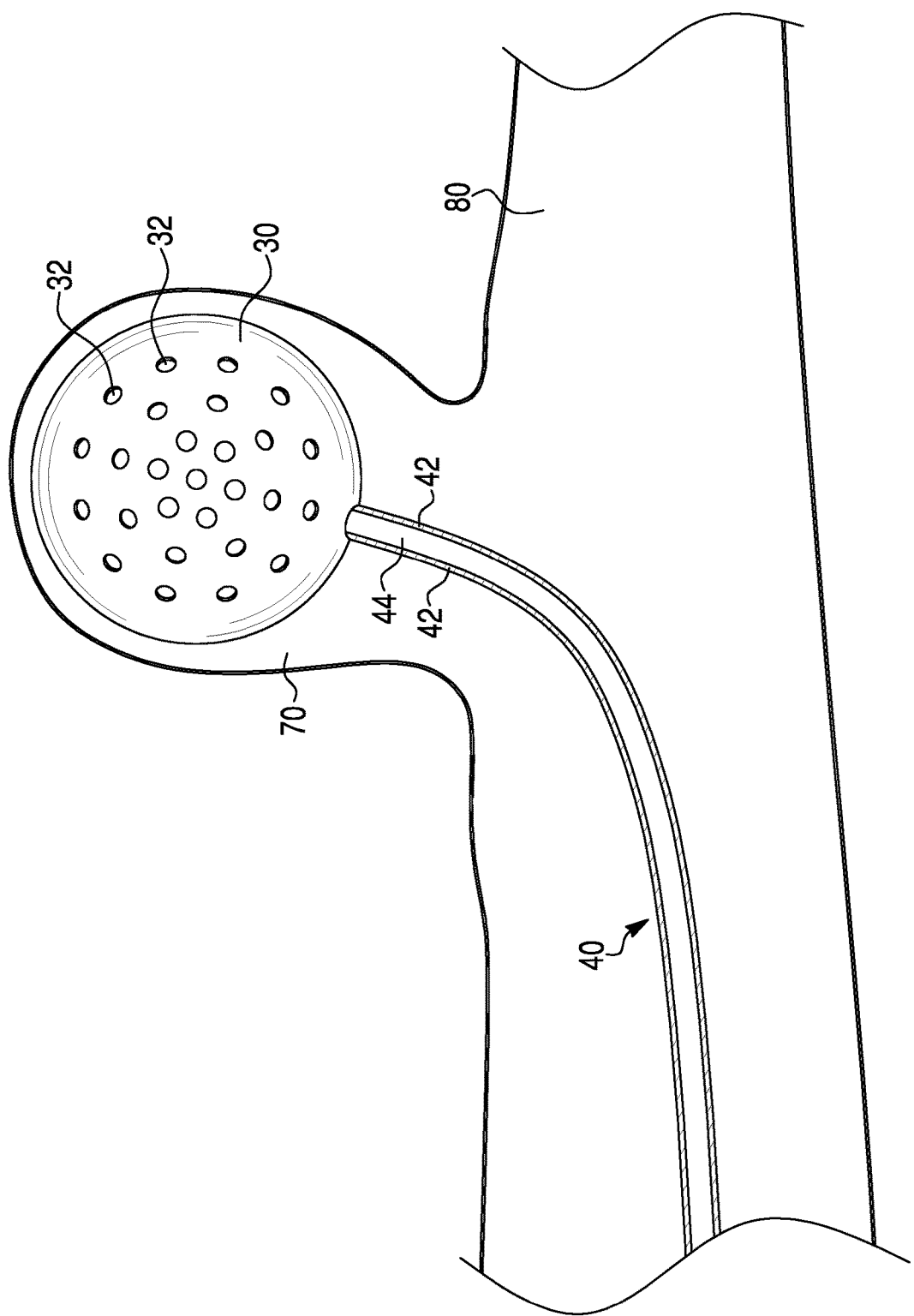
FIG. 2 is a schematic view of the EVAC system of FIG. 1 deployed in a body, according to an embodiment.

An example of system 10 disposed in the body at target site 70 is shown in FIG. 2. Sponge 30 is disposed within target site 70. The distal end of vacuum line 40 is attached to sponge 30 and extends proximally into GI tract 80 and out of the body. A vacuum source (not shown) may be attached to the proximal end of tube 40 to supply a negative pressure to lumen 44 and sponge 30 to draw fluid and materials from target site 70.

A method of forming sponge 30 will now be described. According to an example, sponge 30 may be formed by electrospinning. Additional materials, such as growth factors, antibiotics, and/or other treatment improving materials, may be mixed with the scaffold material prior to electrospinning sponge 30. Unlike traditional stents, which are coated by growth factors or antibiotics after the stent is formed, the material used to form the scaffold of sponge 30 (e.g., the polymer) is mixed with the growth factors or antibiotics before the scaffold is produced, including any material that may promote healing and/or may prevent the growth of microbial matter (e.g., harmful microbes). An amount of eluting material to material used to form sponge 30 may be approximately 1:5 to 1:20.]] According to the example, the polymer and eluting material mixture may be electrospun, forming a sponge 30 having openings 32 in fluid communication with channels.

Sponge 30 may be post-processed by cutting sponge into various shapes described herein. Additional post-processing may include introducing a recess into sponge 30 into which vacuum tube 40 may be introduced and fixed via, e.g., adhesive, sutures, or the like. Sponge 30 may also be cut approximately in half and channels may be formed in each side of sponge 30 to correspond to a branched end of vacuum tube 40. The branched end of vacuum tube 40 may rest in the channels, and sponge 30 may be reassembled using, e.g., adhesive, sutures, etc. The branches of tube 40 may provide additional paths through which fluid and/or materials taken up by sponge 30 may enter lumen 44, which may decrease the healing time of target site 70. It will be understood that this post-processing procedure may be carried out after any method of forming sponge 30.

According to another embodiment, sponge 30 may be formed using a polymer and/or a polymer mixture (e.g., including a polymer and one or more eluting materials) and may be formed into sponge 30 by casting or three-dimensional (3D) printing. As an example, a 3D printer may be programmed to dispense the polymer mixture in a pattern which forms openings, holes, or pores 32 within sponge 30.

In this manner, the shape and/or the size of openings may be controlled. A die may be used to cast sponge 30 with openings. Die casting and/or 3D printing of sponge 30 may form openings, holes, or pores 32 of approximately uniform shapes and/or sizes in sponge 30.

According to yet another embodiment, sponge 30 may include a hygroscopic material, such as a hydrogel, cellulose, or other superabsorbent polymers, such as ply(n-isopropylacrylamide) (PNIPAM), copolymers of PNIPAM, polyacrylic acid, polyacrylamide, polyurethane foam, polyacrylic acid and polyacrylates, carboxy-methyl cellulose, partially cross-linked water swellable polymers such as polyethylene oxide and polyacrylamide, isobutylenemaleic acid copolymer, and the like. Sponge 30 may be made using any method described herein, and may contain one or more additives in some instances. These materials may allow sponge 30 to be introduced in a low profile or compressed state by dehydrating sponge 30 before insertion to the body. Once inserted, sponge 30 may expand when contacted by fluid. For example, a fluid may be introduced to sponge 30 at target site 70 via a catheter or other associated tool, or via lumen 44. Alternatively, or additionally, fluid at target site 70 may assist sponge 30 in expanding from the dehydrated state to an expanded state. Once sponge 30 is expanded, the fluid may be removed from target site 70 using vacuum tube 40.

According to another embodiment, sponge 30 may include a thermoresponsive polymer, such as poly(n-isopropylacrylamide) (PNIPAM), copolymers of PNIPAM, polyacrylic acid, and/or polyacrylamide. Similar to sponge 30 including the hygroscopic material, sponge 30 including the thermoresponsive polymer may expand from the low profile or compressed state. Before expanding, sponge 30 may be compressed such that openings 32 are closed and/or are compressed, such that openings 32 are not in fluid connection. When sponge 30 is introduced to target site 70, sponge 30 may expand to the expanded state as sponge 30 is heated above a temperature threshold of approximately 30 degrees C., or approximately 35 degrees C. by heat from the body. The temperature threshold is not limited to these temperatures, and the temperature threshold may be modified through co-polymerization of sponge 30 with other polymers and/or the incorporation of the various materials to be eluted from sponge 30. Once sponge 30 expands, openings 32 may be in fluid connection, allowing fluid to be received by sponge 30. It will be understood that the materials are not limited to thermoresponsive or hygroscopic materials. In some embodiments, the material of sponge 30 may use the pH of the body, a chemical produced in the body (e.g., at target site 70), and/or any other property of the material of sponge 30 to expand sponge 30 from the compressed state to the expanded state.

Another example of forming a sponge may include saturating a material with crystals. For example, a material that is water insoluble, e.g., silicone and/or any material that includes variable mechanical properties, such as a softness or a stiffness of the material, may be mixed with crystals that are water soluble, such as sugar, salt, or any material including crystals soluble in water but which are insoluble in nonorganic solvents. According to an example, Sylgard silicone may be mixed with 10% by weight of a cross-linker to form a silicone mixture. This silicone mixture is water insoluble. The silicone mixture may then be mixed with the water soluble material. A ratio of the water insoluble material to the water soluble material is approximately 50% by mass. Once the water insoluble material is sufficiently saturated with the water soluble material, the mixture may be cured using, e.g., a curing oven. Alternatively, the mixture may settle at the bottom of the mixing container, which may any shape to be formed, e.g., a shape corresponding to a shape of the mixing container. Once the mixture has been cured or settled at the bottom of the mixing container, the resulting hardened mixture of water insoluble material and water soluble material may be placed in a water bath. The water is approximately 50 degrees C. to approximately 100 degrees C., and the cured mixture may remain in the water bath for approximately 12 hours. During this time, the water dissolves substantially all of the water soluble material, creating pores, channels, and/or openings 32 in sponge 30 in areas from which the water soluble material is dissolved. The size and shape of these pores, channels, and/or openings 32 is approximately equal to the size and shape of the crystals of the water soluble material. Once the water soluble material has been dissolved, sponge 30 may be pliable and/or compressible.

A method of using system 10 will now be described. Sponge 30 may be introduced through an orifice (e.g., a natural body orifice) and advanced to target site 70 using a catheter or other known mechanism. Once sponge 30 is disposed at target site 70, a fluid may be supplied to sponge 30 via, e.g., the catheter. Alternatively, the fluid at target site 70 may activate sponge 30 to expand. In the situation where sponge 30 includes a heat activated material, sponge 30 may expand when sponge 30 is heated above a temperature threshold by the body at target site 70. Once sponge 30 has been expanded from the compressed state to the expanded state, vacuum line 40 may be attached to a vacuum source and a negative pressure of approximately 125 mm Hg, or approximately 2.5, may be supplied to sponge 30.

It will be understood that any of the materials, coatings, or eluting materials described herein may be used alone or in combination to form a medical sponge. It will also be understood that features of any of the sponges described herein may be used with any other EVAC system, and/or any other medical system.

While different medical systems have been described, it will be understood that the particular arrangements of elements in these systems are not limited. Moreover, a size, a shape, and/or the materials of the sponges in the EVAC system are not limited. The sponges are used to access and treat a target site within or outside of a GI tract lumen. For example, in certain procedures, performing various medical procedures may be improved by using a sponge having materials, e.g., growth hormones and/or antibiotics, eluted from the sponge at the target site to prevent infection or other medical issues in organs outside the GI tract.

It will be apparent to those skilled in the art that various modifications and variations can be made to the disclosed devices without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical system comprising:
 a single tube defining a lumen, wherein the single tube includes a plurality of branches at a distal end of the tube; and
 a porous body fixed to the distal end of the single tube and configured to be advanced to a target site within a subject, wherein the porous body defines a plurality of openings, wherein the plurality of openings are in fluid connection with the lumen, wherein the porous body includes a first material and a second material, wherein the second material is configured to elute from the porous body in the subject, wherein the porous body is fixed to the distal end of the single tube via sutures or an adhesive, wherein the porous body is at a distalmost end of the medical system, and wherein each branch of the plurality of branches rests in a corresponding channel of a plurality of channels of the porous body.

2. The medical system of claim 1, wherein the first material includes a polymer, and wherein the second material includes one or more of a growth factor or an antibiotic.

3. The medical system of claim 1, wherein the first material includes a hygroscopic material, and wherein the porous body is configured to be in a compressed state during insertion to the target site.

4. The medical system of claim 3, wherein the porous body is configured to expand from the compressed state to an expanded state when the porous body contacts fluid.

5. The medical system of claim 3, wherein the plurality of openings are fluidly disconnected from each other when the porous body is in the compressed state, and the plurality of openings are in fluid connection as the porous body expands from the compressed state to an expanded state.

6. The medical system of claim 1, wherein the first material includes a thermoresponsive material, and wherein the porous body is configured to be in a compressed state during insertion to the target site.

7. The medical system of claim 6, wherein the porous body is configured to expand from the compressed state to an expanded state when the porous body is heated to a temperature above a temperature threshold by body heat.

8. The medical system of claim 1, wherein the porous body includes nanoparticles having antimicrobial properties.

9. The medical system of claim 1, wherein the plurality of openings are formed using a crystalline material, and wherein a size and a shape of the openings is approximately equal to a size and a shape of a crystal of the crystalline material.

10. The medical system of claim 1, further comprising a vacuum source, wherein the vacuum source is connected to the single tube and is configured to supply a negative pressure to the lumen of the single tube and the porous body.

11. The medical system of claim 3, wherein the porous body is configured to compress from an expanded state to the compressed state when the porous body is dehydrated before insertion to the body.

12. A medical system comprising:
a single tube defining a lumen, wherein the single tube includes a plurality of branches at a distal end of the single tube; and
a porous body connected to the distal end of the single tube and configured to be advanced to a target site within a subject, wherein the porous body defines a plurality of openings, wherein the plurality of openings are in fluid connection with the lumen, wherein the porous body includes a first material and a second material, wherein the second material is configured to elute from the porous body in the subject, wherein the porous body is configured to expand from a compressed state to an expanded state when the porous body is heated above a temperature threshold of 30° ° C. or 35° C. by body heat, wherein the porous body is connected to the distal end of the single tube via sutures or an adhesive, and wherein each branch of the plurality of branches rests in a corresponding channel of a plurality of channels of the porous body.

13. The medical system of claim 12, wherein the porous body is coated with silver nanoparticles.

14. The medical system of claim 12, wherein a size of the plurality of openings is approximately 50 μm to approximately 1 mm in diameter.

15. The medical system of claim 12, wherein the first material includes a thermoresponsive material.

16. A medical system comprising:
a single tube defining a lumen, wherein the single tube includes a plurality of branches at a distal end of the single tube; and
a porous body fixed to the distal end of the single tube and configured to be advanced to a target site within a subject, wherein the porous body defines a plurality of openings, wherein the plurality of openings are in fluid connection with the lumen, wherein the porous body includes a first material and a second material, wherein the second material is configured to elute from the porous body in the subject, wherein the first material is responsive to a pH of the body to transition the porous body from a compressed state to an expanded state, wherein the porous body is at a distalmost end of the medical system, and wherein each branch of the plurality of branches rests in a corresponding channel of a plurality of channels of the porous body.

17. The medical system of claim 16, wherein the first material is a polymer, wherein the second material includes a growth factor and an antibiotic, and wherein the first material and the second material are mixed together.

18. The medical system of claim 16, wherein the distal end of the single tube is positioned within a recess of the porous body and is fixed to the porous body via sutures or an adhesive.

19. The medical system of claim 16, wherein a distalmost end of the single tube is proximal to a distalmost end of the porous body.

20. The medical system of claim 4, further comprising a catheter configured to supply the fluid to the porous body to transition the porous body from the compressed state to the expanded state.

* * * * *